(12) United States Patent
Karmaker et al.

(10) Patent No.: US 7,331,789 B2
(45) Date of Patent: Feb. 19, 2008

(54) METHOD OF MANUFACTURING DENTAL POSTS, OBTURATORS AND RESTORATIONS

(75) Inventors: Ajit Karmaker, Wallingford, CT (US); Arun Prasad, Cheshire, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 443 days.

(21) Appl. No.: 10/774,231

(22) Filed: Feb. 6, 2004

(65) Prior Publication Data

US 2004/0202985 A1 Oct. 14, 2004

Related U.S. Application Data

(60) Provisional application No. 60/445,923, filed on Feb. 6, 2003.

(51) Int. Cl.
*A61C 5/08* (2006.01)
(52) U.S. Cl. .................................................... 433/220
(58) Field of Classification Search ................ 433/220, 433/221, 225, 224
See application file for complete search history.

(56) References Cited

U.S. PATENT DOCUMENTS

| | | |
|---|---|---|
| 3,066,112 A | 11/1962 | Bowen |
| 3,179,623 A | 4/1965 | Bowen |
| 3,194,784 A | 7/1965 | Bowen |
| 3,477,902 A | 11/1969 | Tomasino et al. |
| 3,751,399 A | 8/1973 | Lee, Jr. et al. |
| 3,926,906 A | 12/1975 | Lee, II et al. |

(Continued)

FOREIGN PATENT DOCUMENTS

DE 2744131 A 4/1979

(Continued)

OTHER PUBLICATIONS

PCT Notification of Transmittal of the International Search Report and The Written Opinion of the International Searching Authority, or the Declaration, Date of the Mailing Jun. 17, 2004.

(Continued)

*Primary Examiner*—Melba N. Bumgarner
(74) *Attorney, Agent, or Firm*—Ann M. Knab

(57) ABSTRACT

Dental posts and obturators are manufactured herein having a filling material applied to the apical end of the post and obturator such that the adherence strength between the filling material and the post or obturator is very high. The filling material is adhered to the post and obturator by applying one or more corona or plasma treatments to the surface of the post and obturator and thereafter applying the filling material to the surface-treated post and obturator. The surfaces of the post and obturator are modified by the corona or plasma treatments to create a highly adherent surface for the application of the filling material thereto.

Figure 1:
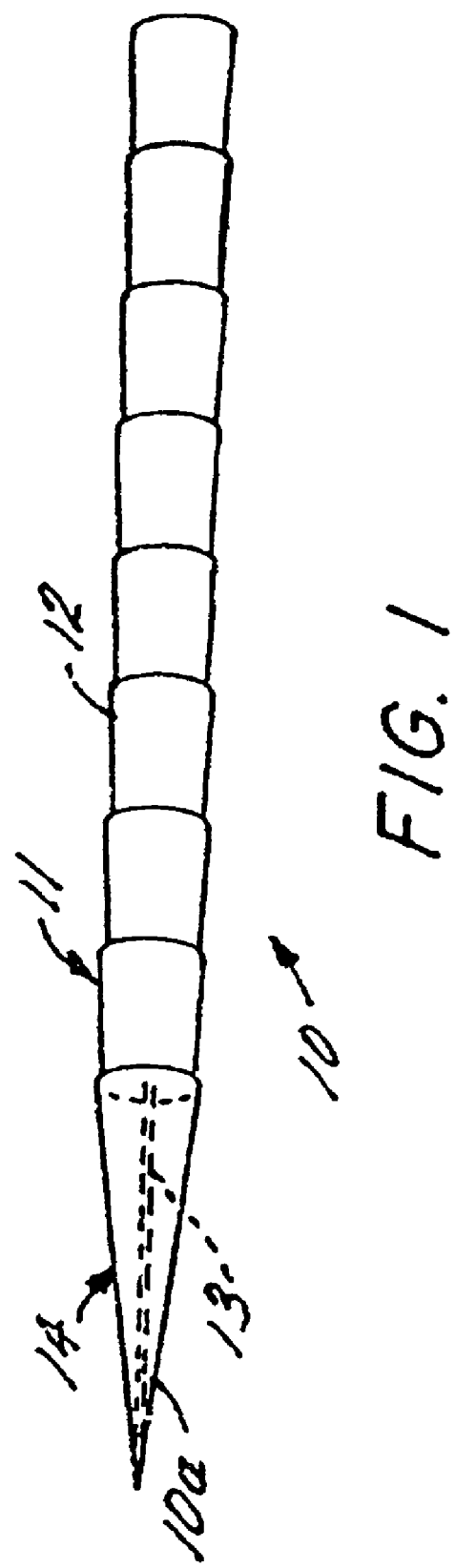

Dental restorations are manufactured herein wherein a veneer is applied to a dental substructure and the adherence strength of the veneer to the dental substructure is very high. The veneer is adhered to the dental substructure by applying one or more corona or plasma treatments to the surface of the dental substructure and thereafter applying the veneer to the dental substructure. The surface of the dental substructure is modified by the corona or plasma process to create a highly adherent surface for the application of the veneer thereto.

35 Claims, 3 Drawing Sheets

U.S. PATENT DOCUMENTS

| | | | |
|---|---|---|---|
| 4,544,359 A | 10/1985 | Waknine | |
| 4,547,531 A | 10/1985 | Waknine | |
| 4,717,341 A | 1/1988 | Goldberg et al. | |
| 4,894,012 A | 1/1990 | Goldberg et al. | |
| 5,051,586 A | 9/1991 | Sabreen | |
| 5,183,701 A | 2/1993 | Jacobs et al. | |
| 5,188,800 A | 2/1993 | Green, Jr. et al. | |
| 5,276,068 A | 1/1994 | Waknine | |
| 5,480,301 A | 1/1996 | Farzin-Nia et al. | |
| 5,564,929 A | 10/1996 | Alpert | |
| 5,829,979 A | 11/1998 | Kobashigawa et al. | |
| 5,873,725 A | 2/1999 | Perler et al. | |
| 5,919,044 A | 7/1999 | Sicurelli, Jr. et al. | |
| 6,030,220 A | 2/2000 | Karmaker et al. | |
| 6,033,582 A * | 3/2000 | Lee et al. | 216/37 |
| 6,039,569 A | 3/2000 | Prasad et al. | |
| 6,057,004 A | 5/2000 | Oppawsky et al. | |
| 6,096,156 A | 8/2000 | Morin et al. | |
| 6,200,136 B1 | 3/2001 | Prasad et al. | |
| 6,287,122 B1 * | 9/2001 | Seeram et al. | 433/220 |
| 6,299,438 B1 | 10/2001 | Sahagian et al. | |
| 6,391,940 B1 * | 5/2002 | Blackwell et al. | 523/115 |
| 6,428,319 B1 | 8/2002 | Lopez et al. | |
| 6,439,890 B1 | 8/2002 | Karmaker et al. | |
| 6,447,297 B1 | 9/2002 | Lopez et al. | |
| 2001/0040316 A1 | 11/2001 | Stewart | |
| 2001/0046595 A1 | 11/2001 | Moran et al. | |

FOREIGN PATENT DOCUMENTS

| | | |
|---|---|---|
| DE | 213 573 A | 9/1984 |
| EP | 0 301 765 A2 | 2/1989 |
| EP | 0 580 994 A | 2/1994 |
| WO | WO 2004/071327 A1 | 8/2004 |

OTHER PUBLICATIONS

Kaplan, SL; Rose, PW; "Plasma Surface Treatment of Plastics to Enhance Adhesion", Int. J. Adhesion and Adhesives, vol. 11, No. 2, Apr. 1991, pp. 109-113.

Chang, Tao C., Plasma Surface Treatment in Composites Manufacturing, Journal of Industrial Technology, vol. 15, No. 1—Nov. 1998 to Jan. 1999, pp. 2-7.

Garbassi, F., Morra M., Occhiello, E., Polymer Surfaces from Physics to Technology, pp. 224-229.

Kaplan S. L., Rose P.W., Plasma Surface Treatment of Plastics to Enhance Adhesion, Plasma Science, Inc., Belmont, CA.

\* cited by examiner

METHOD OF MANUFACTURING DENTAL POSTS, OBTURATORS AND RESTORATIONS

CROSS-REFERENCE TO RELATED APPLICATIONS

This application claims priority to U.S. Provisional Application No. 60/445,923, filed Feb. 6, 2003, which is incorporated herein by reference.

FIELD OF THE INVENTION

This invention relates to the manufacture of posts and obturators and more specifically to the manufacture of single-unit posts and obturators having a filling material attached thereto. The invention further relates to the bonding of filling materials to posts and obturators and to the bonding of veneers to dental understructures.

BACKGROUND OF THE INVENTION

Gutta percha and gutta percha-like natural and synthetic rubbers and thermoplastics do not adhere well to posts and obturators. Many posts and obturators are made of glass fiber-reinforced dental resins and their components are dissimilar to gutta percha and other thermoplastics that are molded onto the appliance. The surface wettability of the post and obturator are low due to at least two reasons: a) the matrix resins used to make the fiber-reinforced composite of the post and obturator are of a hydrophobic rather than hydrophilic nature; and b) the surface is precured leaving an insufficient number of unsaturated chemical bonding for further reaction. Both of these factors will work against good adhesion between the post or obturator and the gutta percha or other hydrophobic thermoplastic or other material.

Similar bonding problems exist between dental substructure materials and overlayer veneer materials. The general practice is to partially light cure the fiber-reinforced composite substructure and to keep an oxygen-inhibited layer for better wetting of the subsequent overlayer materials. However, the oxygen-inhibited layer itself is expected to be weak in strength and consequently poor adhesion along this layer is likely. To eliminate this weak layer, a higher degree of conversion in the absence of oxygen is required. This practice, however, limits the availability of unsaturated bonds on the surface for any future adhesive procedures.

The application of additional layers of material to an understructure has been taught in the art whereby plasma deposition is used to apply the layers to the understructure. U.S. Pat. No. 5,873,725 is directed to a dental post having a layer of ceramic material deposited over and bonded to the outside surface to facilitate adhesion of the post to a dental adhesive. The surface of the post is first roughened to increase the surface area of the post and thereafter a layer of ceramic material is applied by sputtering or plasma spray deposition. The layer of ceramic material does not alter the surface of the post, but adds an additional layer of material, namely ceramic, to the post. Similarly, U.S. Pat. No. 5,480,301 is directed to an orthodontic appliance whereon particles of stainless steel, ceramic, ceramic-metal composite, or metal-metal composite materials are applied to the surface of the orthodontic appliance by plasma spray coating, arc spray coating, flame spray coating or vacuum sputtering.

It has also been known to use plasma deposition for enhancing the bond strength of fibers to the matrix material in a fiber reinforced composite material. Commonly owned U.S. Pat. No. 6,200,136 is directed to a fiber-reinforced dental bridge material wherein the material comprises fibers embedded in a polymeric base material. In order to enhance the bond between the reinforcing fibers and the base material, thereby enhancing the reinforcing effect, the patent teaches silanizing or otherwise treating the fibers by etching, chemically grafting, plasma treating, or ion-bombarding. U.S. Pat. No. 5,829,979 is directed to a reinforcing material for dental appliances and prostheses. The reinforcing material is sometimes pretreated with a cold gas plasma or other such process that will increase the wetability and chemical activity of the material and thereby enhance the ability of the material and the resin to adhere.

The aforementioned prior art has been limited to bonding processes used during the impregnation of fibers in a polymeric matrix or to the actual addition of layers to an understructure.

Attempts have been made to improve the bonding between posts and obturators and gutta percha by applying silane or a silane/resin mixture to the post and obturator. Nevertheless, the bond is still quite weak.

It is desirable to increase the bond strength between posts and obturators and gutta percha or gutta percha-like natural or synthetic rubbers and thermoplastics. It would be beneficial to improve the bond strength between dental substructures and composite veneering materials.

SUMMARY OF THE INVENTION

Dental posts and obturators are manufactured herein having a filling material applied to the apical end of the post and obturator such that the adherence strength between the filling material and the post or obturator is very high. The filling material is adhered to the post and obturator by applying one or more corona or plasma treatments to the surface of the post and obturator and thereafter applying the filling material to the surface-treated post and obturator. The surfaces of the post and obturator are modified by the corona or plasma treatments to create a highly adherent surface for the application of the filling material thereto.

Dental restorations are manufactured herein wherein a veneer is applied to a dental substructure and the adherence strength of the veneer to the dental substructure is very high. The veneer is adhered to the dental substructure by applying one or more corona or plasma treatments to the surface of the dental substructure and thereafter applying the veneer to the dental substructure. The surface of the dental substructure is modified by the corona or plasma process to create a highly adherent surface for the application of the veneer thereto.

DESCRIPTION OF THE INVENTION

As will be appreciated, the present invention provides a method of bonding gutta percha and gutta percha-like thermoplastic materials to posts and obturators to provide a combined endodontic post and tip of filling material in a single unit, or an endodontic obturator having filling material in an integral, single unit.

FIG. 1 shows a post unit 10 comprising a post section 11 and a cone or tip section 14. Post section 11 contains a main body 12 and a carrier or apical portion 13. Carrier portion 13 is preferably an extension of main body 12 of post section 111 and may be of very fine diameter to accommodate tip section 14 of filling material. Tip section 14 comprises a flexible rod or cone of biocompatible material for filling the apex of the canal. The cone of biocompatible filling material is attached to carrier portion 13 of post section 11 at the apical end 10a of post unit 10. Carrier 13 may be formed during the actual manufacture of main body 12 or thereafter by grinding, cutting or similar means.

Figure 2:
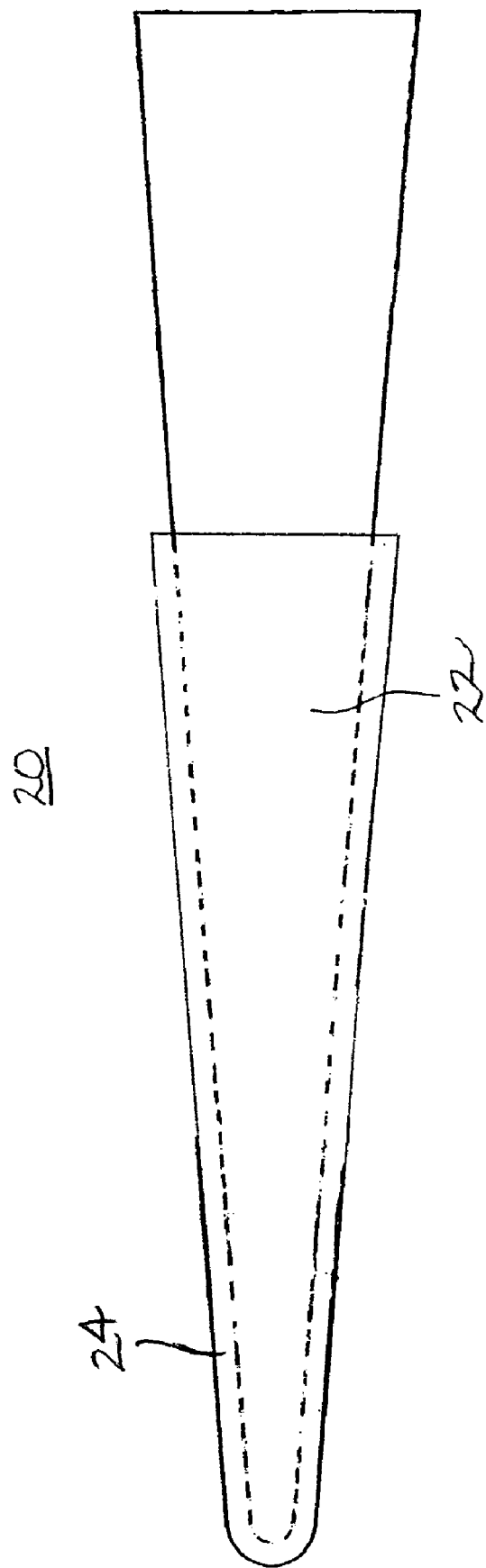

FIG. 2 shows an obturator 20 having a carrier 22 with a cone of biocompatible filling material 24 attached thereto. As shown in the drawings, post section 10 and carrier 22 are each tapered to provide ease of placement into the canal.

The filling material may be any known filling material including, but not limited to, gutta-percha, thermoplastic, thermoset, chemoplastic, or other resin or polymeric material. Copending, commonly assigned pending U.S. patent application Ser. No. 10/164,512 filed Jun. 6, 2002; Ser. No. 10/633,610 filed Aug. 1, 2003; Ser. No. 10/633,612 filed Aug. 1, 2003; Ser. No. 10/279,609 filed Oct. 24, 2002; Ser. No. 10/304,371 filed Nov. 26, 2002; Ser. No. 10/465,416 filed Jun. 18, 2003; and commonly assigned U.S. Pat. Nos. 6,428,319, 6,447,297 and 6,439,890 are directed to posts, obturators and filling materials used for filling root canals, and are hereby incorporated by reference.

Examples of polymeric filling materials include, but are not limited to, polyacrylates/methacrylates, polyurethanes, polypropylenes, polyethylenes, polyamides, fluoropolymers, polyesters, polyphosphazenes, polyanhydrides, polysulfides, polyethers, epoxies, polycarbonates, polystyrenes, polyisoprenes, polybutadienes, polyphenylene oxides, silicone rubbers, polylactides, polyglycolides, polycaprolactones, polyamides, polyesteramides, polyorthoesters, polydioxanones, polyacetals, polyketals, polyorthocarbonates, polyhydroxybutyrates, polyhydroxyvalerates, polyalkylene oxalates, polyethylene oxides, polyalkylene succinates, poly(malic acid) polymers, polymaleic anhydrides, poly(methylvinyl) ethers, poly(amino acids), chitin, chitosan, polyamides, polyesters, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates (hereinafter abbreviated to "UDMA", triethylene glycol dimethacrylate (hereinafter abbreviated "TEGDMA"), polyethylene glycol dimethacrylate (hereinafter abbreviated "PEGDMA"), urethane dimethacrylate (hereinafter abbreviated "UDMA"), hexane diol dimethacrylate (hereinafter abbreviated "1,6 HDDMA") and polycarbonate dimethacrylate (hereinafter abbreviated "PCDMA") and copolymers, terpolymers, or combinations or mixtures thereof.

Examples of polyacrylates include, but are not limited to, polymethyl methacrylate, polyhydroxy ethyl methacrylate, or hydroxy ethyl methacrylate (HEMA). Examples of fluoropolymers include, but are not limited to, Teflon® PTFE or Teflon® PFA.

Examples of polyesters include, but are not limited to, polylactic acid, glycolide, polycaprolactone or a co-polymer thereof. An example of silicone rubber is polysiloxane.

Preferred filling materials for application to the tip of the post or obturator are polylactides, polyglycolides, polycaprolactones, and copolymers thereof.

A filler may also be included in the filling material. The filler may include inorganic and organic particulates and fibrous fillers known in the art including, but are not limited to, silica, silicate glass, quartz, zinc oxide, barium sulfate, barium silicate, strontium silicate, barium borosilicate, strontium borosilicate, borosilicate, lithium silicate, amorphous silica, bismuth compounds such as BiOCl, ammoniated or deammoniated calcium phosphate and alumina, zirconia, tin oxide, and titania, among other conventional fillers such as those disclosed in commonly assigned U.S. Pat. Nos. 4,544,359 and 4,547,531 to Waknine (which are incorporated herein by reference). Some of the fillers also act as radiopaque/high refractive index materials, such as apatites, silica glass fillers, calcium silicate based fillers, hydroxyapatites, barium sulfate, bismuth subcarbonate, ytterbium oxide, ytterbium fluoride, ytterbium iodine, bismuth oxide, bismuth fluoride, barium oxide, and tantalum oxide. Fibrous fillers also include, but are not limited to, include glass, ceramic, metal, carbon, graphite, polymeric such as cellulose, polyamide, aramid, polyester, polyaramid, acrylic, vinyl and modacrylic, polyolefin, polytetrafluorethylene, mixtures thereof, as well as other fibers known in the art.

A bioactive substance may be combined with the polymer used in the filling material. The bioactive material may include any substance or metabolic precursor thereof, which is capable of promoting growth and survival of cells, tissues, and bone. Suitable bone growth promoting substances include but are not limited to bioglass, calcium phosphate, Portland cement, hydroxyapatite, tricalcium phosphate, a di- or polyphosphonic acid, an anti-estrogen, a sodium fluoride preparation, a substance having a phosphate to calcium ratio similar to natural bone, calcium hydroxide, other suitable calcium-containing compounds, and the like. A bone growth promoting substance may be in the form of a particulate or fiber filler in nano, micro or macro form, or mixtures thereof, bone chips, bone crystals or mineral fractions of bone and/or teeth, a synthetic hydroxyapatite, or other suitable form. The bioactive filler may be present in an amount of up to about 90 percent by weight.

The filling material may include additives typical in the dental field such as plasticizing, antibiotic, cariostatic, antibacterial, or other anti-inflammatory, biologically active or therapeutic materials.

The post or obturator section may be fabricated of any material to provide a flexible apical portion and a more rigid endodontic and/or coronal or supracoronal portion, such as metal, plastic, ceramic, polymeric, composite, or other material suitable for placement in the mouth. Composite materials include but are not limited to filler reinforced composite materials and fiber reinforced composite materials comprising the reinforcing component in a polymeric matrix material such as those composite materials listed in U.S. Pat. Nos. 4,717,341 and 4,894,012 to Goldberg et al., U.S. Pat. No. 6,039,569 to Prasad et al., U.S. Pat. No. 6,030,220 to Karmaker et al, U.S. Pat. No. 5,564,929 to Alpert, and U.S. Pat. No. 5,919,044 to Sicurelli, Jr. et al., all of which are hereby incorporated by reference. The fiber reinforced composite material may comprise fibers in the form of long, unidirectional, continuous filaments which are preferably at least partially aligned and oriented along the longitudinal dimension of the component with alignment normal or perpendicular to that dimension also possible. The fibers may be of uniform or random length, unidirectional or multidirectional, or randomly dispersed, and may be as short as about 3 to about 4 millimeters (mm) or shorter. The fibers may also be in the form of fabric as set forth in copending Ser. No. 10/184,353 filed Jun. 26, 2002, and may include any of the attributes of the post described therein, the contents all of which are hereby incorporated by reference.

Due to the improved structural integrity, the amount of fibers in the structural component preferably equals at least about 20% by weight (wt %) and preferably about 20 wt % to about 70 wt %. Possible reinforcing fibers, which are preferably used in accordance with U.S. Pat. Nos. 4,717,341 and 4,894,012 to Goldberg et al. (which are herein incorporated by reference), include glass, ceramic, metal, carbon, graphite, polymeric such as cellulose, polyamide, aramid, polyester, polyaramid, acrylic, vinyl and modacrylic, polyolefin, polytetrafluorethylene, mixtures thereof, as well as other fibers known in the art. One preferred version of the device is comprised of unidirectional microfilamentous glass fibers bundled in a resin matrix.

The polymeric matrix is selected from those known in the art of dental materials, including, but not limited to, polyamides, polyester, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates (hereinafter abbreviated to PUDMA), and the like. Preferred polymeric matrix materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Waknine (which are herein incorporated by reference). An especially preferred methacrylate monomer is the condensation product of bisphenol A and glycidyl methacrylate, 2,2'-bis [4-(3-methacryloxy-2-hydroxy propoxy)-phenyl]-propane (hereinafter abbreviated "BIS-GMA").

The polymer matrix, which typically includes polymerization initiators, polymerization accelerators, ultra-violet light absorbers, anti-oxidants, fluorescent whitening agents, free radical initiators, and/or other additives well known in the art, may be visible light curable, self-curing, dual curing, or vacuum, heat, or pressure curable compositions, as well as any combination thereof. Heat and pressure or vacuum curable compositions include a heat cure initiator such as benzoyl peroxide, 1,1'-azobis(cyclohexanecarbo-nitrile) or other free radical initiators. The preferred polymeric matrix is a light and heat curable matrix, wherein light effects partial cure of the polymer matrix, while final curing is by heat under controlled atmosphere.

Fillers may be present in addition to or instead of fibers in an amount up to about 80 wt %, and preferably about 70 wt %. If fibers are present, the amount of filler is present in an amount of up to about 30 wt % of one or more fillers known in the art and used in dental restorative materials. Suitable fillers include those capable of being covalently bonded to the polymeric matrix itself or to a coupling agent that is covalently bonded to both. Fillers include silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania, among other conventional fillers such as those disclosed in commonly assigned U.S. Pat. Nos. 4,544,359 and 4,547,531 to Waknine (which are incorporated herein by reference), while possible coupling agents include silanes, zirconates, and titanates. If the post is manufactured from a composite material, it is preferably in completely cured or hardened state. However, some uncured residual monomers may be still present in the hardened post.

Examples of metals useful as post or obturator section include but are not limited to metals or alloys of Pd, Pt, Rh, Ir, Au, Ag, Ti, Co, Mo and mixtures thereof such as AgPd, AuPtPd, TiAlFe, TiAlV, CoCrMo, stainless steel and brass. Ceramic materials useful in the fabrication of the post or obturator section include but are not limited to alumina, zirconia, mullite, spinel, porcelain, titania, lithium disilicate, leucite, amorphous glass, lithium phosphate, and combinations thereof, or any high strength ceramic material which can withstand the stresses created in the mouth.

In accordance with one method of manufacture herein, the post or obturator, which include a main body and carrier, is manufactured by any known method in the art and depending upon the material used for the manufacture of posts and obturators. Such methods include but are not limited to matched die processes, autoclave molding, resin injection molding (RIM), sheet, dough and bulk molding, press molding, injection molding, reaction injection molding, resin transfer molding (RTM), compression molding, open molding, hand rolling, dipping and rolling, pressing, extrusion, pultrusion and filament winding. As discussed above, the post or obturator is formed into a rod-shaped unit or main body having a very fine or thin apical end or carrier, when used as a post, or having a tapered body, when used as an obturator. The final shape of the post or obturator may be formed simultaneously during the manufacturing process thereof.

Alternatively, a rod shaped material may be manufactured and thereafter shaped by grinding, cutting, milling or the like into the desired shape and size.

The post may be provided in an opaque tooth color or it may be colored similar to a tooth's pulp for enhanced esthetics. The post may include an appropriate amount of raadiopaque material such as titanium oxide, bismuth oxychloride, barium sulfate, and similar materials known in the dental industry to insure x-ray documentation which may be added to the post material during manufacture thereof.

After post section 11 has been manufactured, carrier 13 of post section 11 is then coated with a filling material, as described above, to obtain cone section 14 thereon. Likewise, after carrier 22 of obturator 20 has been manufactured, it is coated with filling material 24. The filling material may be applied by any known means such as dipping, injection molding, hand rolling, spraying, and the like. The filling material may be any suitable material used for filing root canals as described above.

In order to optimally bond the filling material to the post or obturator, the post or obturator is exposed to a plasma or corona treatment. The plasma or corona treatment modifies the surface of the post and obturator to create an excellent bonding surface. In both treatments ionized species such as ions, radicals, electrons and molecules in excited states are formed by high-energy electromagnetic fields. The surfaces modified by the ionized species promote better wetting of the subsequent molded or layered materials applied to the material of the post and obturator.

The corona system works at low temperature in atmospheric pressure, whereas the cold plasma requires a vacuum chamber and gas field, to maintain the appropriate pressure and composition of gaseous mixture.

The methods described herein involve the application of energetic ion beams onto the surface of the post or obturator. The ions break chemical bonds near the surface of the post or obturator material, thereby making it more reactive for bonding to the gutta percha and gutta percha-like materials without changing the properties of the material. Plasmas provide a low temperature environment using electrical energy rather than heat to promote chemical reactions. Plasmas eliminate the dangers associated with cleaning up of chemicals and are environmentally friendly, with no liquid waste requiring costly disposal. Moreover, the ion bombardment process is a one-step process that requires little or no supervision.

In cold plasma treatment used herein, gases used include, but are not limited to, air, nitrogen, argon, oxygen, nitrous oxide, helium, tetrafluoromethane, water vapor, carbon dioxide, methane, and ammonia. Each gas produces a unique plasma composition and results in different surface properties.

In another embodiment herein, the application of plasma and corona treatments may be used in bonding veneer materials to understructures using the same materials as those described above for the posts and obturators. The treatments are the same as described above for bonding gutta and gutta percha-like natural or synthetic rubbers, thermoplastics and the like to the posts and obturators. Treating the understructure with a corona or plasma treatment increases the bond strength between the understructure and the veneer. Veneers may include resins, porcelains and similar materials known and used in the industry.

The corona treatment is preferably carried out in atmospheric air at room temperature. The treatment time can vary depending upon the material of the post or substrate and the material to be applied. Preferably, it ranges for a time period from about a few seconds to about two hours and more preferably from about four seconds to about one hour and most preferably from about six seconds to about thirty minutes.

The plasma treatment is preferably carried out in an oxygen atmosphere at a rate of from about 10 cc/min to about 200 cc/min at a power from about 100 watts to about 600 watts for a time period from about a few seconds to about two hours and more preferably for a time period from about four seconds to about one hour and most preferably for a time period from about six seconds to about thirty minutes.

Most preferably, the plasma treatment is carried out at about 100 cc/min at a power of 400 watts for about 10 minutes. Alternatively, the plasma treatment is carried out in an atmosphere containing a mixture of oxygen and carbon tetrafluoride ($CF_4$) at a rate of about 10 cc/min at a power of 300 watts for about 10 minutes.

In using the process with fiber-reinforced composite materials, there is no need for the formation of an oxygen-inhibited layer on the fiber-reinforced composite materials. Furthermore, the fiber-reinforced composite material surfaces may be fully cured.

The following nonlimiting examples illustrate the invention.

EXAMPLES

Figure 3:
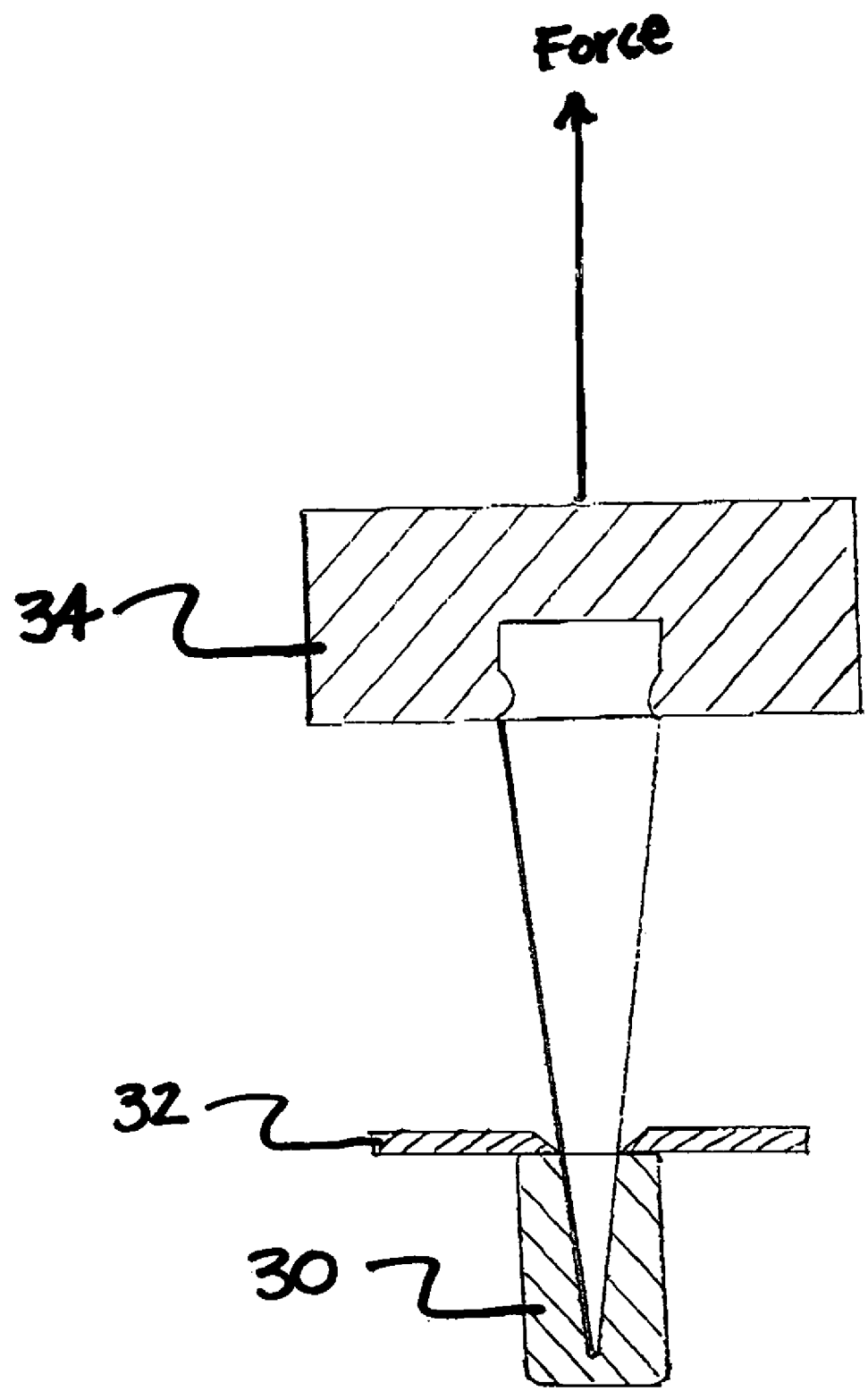

To demonstrate the effect of the corona and plasma treatments on bonding between cured fiber-reinforced composites and gutta percha, a pull out shear test was conducted. A schematic diagram of a specimen used in the pull out test is shown in FIG. 3. Posts manufactured from fiber-reinforced composite posts were coated with a block of gutta percha material. Tapered samples were machine-ground from fiberglass composite rods. The posts were approximately 33 mm in length and tapered at taper of 0.04 mm per mm starting at the tip of the post and tapering for a length of approximately 25 mm, whereat the post extended straight to the end. At the point where the taper ends, a small annular groove is shown. The diameters of the tip or the post and the top end of the post were about 0.18 mm and 0.52 mm, respectively. Gutta percha was injection molded over about 7.7 mm of the length of the post at the tip or tapered end using a specially made mold. The molded gutta percha block did not expose the tip of the post. The molded block was of cylindrical shape and was about 3.0 mm in diameter. A pullout test was carried out using an ATS test machine (Tinius Olsen, Horsham, Pa.) at tensile mode with a test speed of 0.5 mm/min. As shown in FIG. 3, during the test, the molded gutta percha block 30 was supported against a metal vice 32 while the other end of the post was gripped in the upper jaw 34 of the machine. The average embedded post surface of the tapered post was about 8.48 $mm^2$. Force was applied upward from the post as shown in the Figure. To calculate shear strength, the pullout force (the force required to pull the post from the gutta percha block) was divided by the post surface area.

For comparison, in one set of samples, the gutta percha was applied after no surface treatment and in another set of samples, the post was treated using conventional methods, i.e., coating with a silane, prior to the application of gutta percha. In accordance with the invention, gutta percha was applied after treating the posts with a plasma or corona treatment. For the set of samples treated with plasma, two different mixtures were used. One consisted of a mixture of oxygen and carbon tetraflouride, applied at a rate of 10 cc/min, for ten minutes at a power of 300 watts and a second mixture consisted of oxygen, applied at 100 cc/min for ten minutes at a power of 300 watts. For application of the corona treatment, a Plasma-Jet® system (commercially available from Corotec Corp., Farmington, Conn.) was used to treat the samples. The corona treatment involved the application of an energetic ion beam in the presence of atmospheric air. The substrate was slowly moved under the beam at a low speed (about 5 mm/sec). The process can be repeated several times in order to optimize the bond strength.

The results are shown in Table 1 below. As shown in the Table, for the post having no treatment prior to the application of the gutta percha, the force required to remove the gutta percha from the post was 2.74 pounds. For a post treated with silane prior to the application of gutta percha, the force required to remove the gutta percha was 3.3 pounds. For the posts treated with plasma prior to application of the gutta percha, the results were 4.38 and 4.92 pounds. For the posts treated with one corona treatment using the Plasma-Jet®, the results were 4.3. For the posts treated with three corona treatments using the Plasma-Jet@, the results were 6.4, a 94% increase compared to the silane-treated samples having no corona treatment. The application of plasma or corona to the post prior to the application of gutta percha greatly improves the bond strength of the gutta percha to the post.

After the pullout test, the surface of the post was observed by a light microscope. For the plasma-treated post, under the microscope, a thin layer of gutta percha still adhered to the post, was observed. This indicates that cohesive failure occurred inside the gutta percha, not between the gutta percha and the post, evidencing the extremely strong bond between the gutta percha and the post. In comparison, the surface of the non-treated or silane-treated post showed no evidence of a layer of gutta percha, indicating adhesive failure during the pullout test.

TABLE 1

| Example | Treatment | Average Pullout Force (lbs) | Average Pullout Force (N) | Average Shear Strength MPa |
|---|---|---|---|---|
| 1 | None | 2.74 ± .09 | 12.22 | 1.44 |
| 2 | Silane | 3.3 ± .3 | 14.72 | 1.74 |
| 3 | Plasma - mixture of $O_2$ and $CF_4$ at 10 cc/min, for 10 min at 300 watts | 4.38 ± .27 | 19.53 | 2.30 |

TABLE 1-continued

| Example | Treatment | Average Pullout Force (lbs) | Average Pullout Force (N) | Average Shear Strength MPa |
|---|---|---|---|---|
| 4 | Plasma - O₂ at 100 cc/min, for 10 min at 400 watts | 4.92 ± .71 | 21.84 | 2.58 |
| 5 | Corona - 1 treatment using the Plasma-Jet ® | 4.3 ± .9 | 19.18 | 2.26 |
| 6 | Corona - 3 treatments using the Plasma-Jet ® | 6.4 ± 1.2 | 28.54 | 3.37 |

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of making a single unit endodontic post or endodontic obturator having filling material attached thereto wherein the post or obturator are used for insertion in a root canal comprising:
   applying a corona or plasma treatment to the surface of the endodontic post or endodontic obturator;
   applying resinous filling material to the surface of the endodontic post or endodontic obturator; and
   wherein the pull out force between the filling material and the endodontic post or endodontic obuturator is at least 56 percent or greater than the pull out force between the filling material and the endodontic post or endodontic obturator which uses no corona or plasma treatment and is at least 30 percent or greater than the pull out force between the filling material and the endodontic post or endodontic obrturator which uses silane treatment prior to application of the filling material to the endodontic post or endodontic obturator.

2. The method of claim 1 wherein the corona treatment takes place in atmospheric air at room temperature.

3. The method of claim 2 wherein the corona treatment takes place in the range of about a few seconds to about two hours.

4. The method of claim 1 wherein the plasma treatment takes place in an atmosphere selected from the group consisting of air, nitrogen, argon, oxygen, nitrous oxide, helium, tetrafluoromethane, tetrafluoride, water vapor, carbon dioxide, methane, ammonia and mixtures thereof.

5. The method of claim 4 wherein the plasma treatment takes place in an atmosphere containing a mixture of oxygen and carbon tetrafluoride.

6. The method of claim 4 wherein the plasma treatment takes place in the range of about a few seconds to about two hours.

7. The method of claim 1 wherein more than one corona or plasma treatment is applied to the surface of the post or obturator.

8. The method of claim 1 wherein the post or obturator is fabricated of a metal, plastic, ceramic, or a composite material.

9. The method of claim 8 wherein the composite material comprises fiber-reinforced composite material, filler-reinforced composite material or a mixture thereof.

10. The method of claim 9 wherein the filler-reinforced composite material comprises silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, titania, or a mixture thereof.

11. The method of claim 8 wherein the composite material comprises a polymeric matrix.

12. The method of claim 11 wherein the polymeric matrix comprises polyamides, polyester, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates, or a mixture thereof.

13. The method of claim 12 wherein the polymeric matrix further comprises polymerization initiators, polymerization accelerators, ultra-violet light absorbers, anti-oxidants, fluorescent whitening agents, or free radical initiators.

14. The method of claim 8 wherein the metal comprises Pd, Pt, Rh, Ir, Au, Ag, Ti, Co, Mo or mixtures thereof.

15. The method of claim 14 wherein the mixtures of metals or alloys comprise AgPd, AuPtPd, TiAlFe, TiAlY, CoCrMo, stainless steel or brass.

16. The method of claim 8 wherein the ceramic comprises alumina, zirconia, mullite, spinel, porcelain, titania, lithium disilicate, leucite, amorphous glass, lithium phosphate, or a combinations thereof.

17. The method of claim 1 wherein the resinous filling material comprises a polymeric material.

18. The method of claim 17 wherein the polymeric material comprises polypropylenes, polyethylenes, polyamides, fluoropolymers, polyesters, polyphosphazenes, polyanhydrides, polysulfides, polyethers, epoxies, polycarbonates, polystyrenes, polyisoprenes, polybutadienes, polyphenylene oxides, silicone rubbers, polylactides, polyglycolides, polycaprolactones, polyanhydrides, polyimides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyethylene oxides, polyacrylates/methacrylates, polyalkylene succinates, poly(malic acid) polymers, polymaleic anhydrides, poly(methylvinyl) ethers, poly(amino acids), chitin, chitosan, polyolefins, polyarylates, polyurethanes, vinyl esters, styrenes, styrene acrylonitriles, ABS polymers, polysulfones, polycarbonates, polyphenylene sulfides, polyarylsulfides, acrylonitrile-butadiene-styrene copolymers, polyurethane dimethacrylates (hereinafter abbreviated to "UDMA", triethylene glycol dimethacrylate (hereinafter abbreviated "TEGDMA"), polyethylene glycol dimethacrylate (hereinafter abbreviated "PEGDMA"), urethane dimethacrylate (hereinafter abbreviated "UDMA"), hexane diol dimethacrylate (hereinafter abbreviated "1,6 HDDMA") and polycarbonate dimethacrylate (hereinafter abbreviated "PCDMA") and copolymers, terpolymers, or combinations or mixtures thereof.

19. The method of claim 1 wherein the resinous filling material comprises a thermoplastic, thermoset, chemoplastic, material or mixture thereof.

20. The method of claim 19 wherein the thermoplastic material comprises gutta-percha.

21. The method of claim 1 wherein the resinous filling material further comprises a filler.

22. The method of claim 21 wherein the filler comprises inorganic or organic fillers.

23. The method of claim 21 wherein the filler comprises particulates or fibrous fillers.

24. The method of claim 23 wherein the fibrous fillers comprise glass, ceramic, metal, carbon, graphite, polymeric such as cellulose, polyamide, aramid, polyester, polyaramid, acrylic, vinyl and modacrylic, polyolefin, polytetrafluorethylene, or mixtures thereof.

25. The method of claim 21 wherein the filler comprises silica, silicate glass, quartz, zinc oxide, barium sulfate, barium silicate, strontium silicate, barium borosilicate, strontium borosilicate, borosilicate, lithium silicate, amorphous silica, bismuth compounds such as BiOCl, ammoniated or deammoniated calcium phosphate and alumina, zirconia, tin oxide, and titania, apatites, glass fillers, calcium silicate, hydroxyapatites, barium sulfate, bismuth subcarbonate, ytterbium oxide, ytterbium fluoride, ytterbium iodine, bismuth oxide, bismuth fluoride, barium oxide, and tantalum oxide.

26. The method of claim 21 wherein the filler comprises a bioactive filler.

27. The method of claim 26 wherein the bioactive filler comprises bioglass, calcium phosphate, Portland cement, hydroxyapatite, tricalcium phosphate, a di- or polyphosphonic acid, an anti-estrogen, a sodium fluoride preparation, a substance having a phosphate to calcium ratio similar to natural bone, or mixtures thereof.

28. The method of claim 26 wherein the bioactive filler comprises bone chips, bone crystals, mineral fractions of bone or teeth, or mixtures thereof.

29. The method of claim 26 wherein the bioactive filler comprises particulate or fibrous filler in nanosize, microsize, macrosize form, or mixtures thereof.

30. The method of claim 1 wherein the resinous filling material further comprises a polymeric resin, additional filler, pigment, dye, antibiotic, cariostatic, antibacterial, anti-inflammatory, biologically active or therapeutic material.

31. A post manufactured by the method of claim 1.

32. The post of claim 31 wherein the resinous material is bonded to the post at a bond strength greater than about 2.3 MPa.

33. An obturator manufactured by the method of claim 1.

34. The obturator of claim 33 wherein the resinous material is bonded to the obturator at a bond strength greater than about 2.3 MPa.

35. A method of making a single unit post or obturator having filling material attached thereto comprising:
   applying a corona or plasma treatment to the surface of the post or obturator; and
   applying resinous filling material to the surface of the post or obturator, wherein the resinous filling material comprises gutta-percha.

* * * * *